US010709149B2

(12) United States Patent
Muller

(10) Patent No.: US 10,709,149 B2
(45) Date of Patent: Jul. 14, 2020

(54) PREPARATION OF COFFEE FRUIT EXTRACTS AND POWDERS

(71) Applicant: KoffeeFruit Pte. Ltd., Singapore (SG)

(72) Inventor: Mark L. Muller, Kailua-Kona, HI (US)

(73) Assignee: KoffeeFruit Pte. Ltd., Singapore (SG)

( * ) Notice: Subject to any disclaimer, the term of this patent is extended or adjusted under 35 U.S.C. 154(b) by 0 days.

(21) Appl. No.: 15/766,738

(22) PCT Filed: Sep. 1, 2016

(86) PCT No.: PCT/US2016/049942
§ 371 (c)(1),
(2) Date: Apr. 6, 2018

(87) PCT Pub. No.: WO2017/040810
PCT Pub. Date: Mar. 9, 2017

(65) Prior Publication Data
US 2018/0289030 A1    Oct. 11, 2018

Related U.S. Application Data

(60) Provisional application No. 62/214,723, filed on Sep. 4, 2015.

(51) Int. Cl.
| | | |
|---|---|---|
| *A23F 5/02* | (2006.01) | |
| *A23L 19/00* | (2016.01) | |
| *A23L 33/105* | (2016.01) | |
| *A23L 2/52* | (2006.01) | |
| *A61Q 19/08* | (2006.01) | |
| *A61Q 19/00* | (2006.01) | |
| *A61K 8/9783* | (2017.01) | |

(52) U.S. Cl.
CPC ........ *A23F 5/02* (2013.01); *A23L 2/52* (2013.01); *A23L 19/01* (2016.08); *A23L 19/03* (2016.08); *A23L 19/07* (2016.08); *A23L 33/105* (2016.08); *A61K 8/9783* (2017.08); *A61Q 19/00* (2013.01); *A61Q 19/08* (2013.01); *A61K 2236/00* (2013.01)

(58) Field of Classification Search
CPC . A23F 5/02; A23L 19/01; A23L 19/03; A23L 19/07; A23L 2/52; A61K 8/9783; A61K 2236/00; A61Q 19/00; A61Q 19/08
See application file for complete search history.

(56) References Cited

U.S. PATENT DOCUMENTS

| | | |
|---|---|---|
| 2,557,294 A | 6/1951 | Kellogg |
| 3,725,076 A | 4/1973 | Stefanucci et al. |
| 4,112,130 A | 9/1978 | Gupta |
| 4,316,916 A | 2/1982 | Adamer |
| 5,252,061 A | 10/1993 | Ozer et al. |
| 5,624,699 A | 4/1997 | Lang |
| 6,113,908 A | 9/2000 | Paton et al. |
| 6,159,512 A | 12/2000 | Reyes |
| 6,231,866 B1 | 5/2001 | Mann |
| 6,235,721 B1 | 5/2001 | Ghosal |
| 6,268,007 B1 | 7/2001 | Geromini et al. |
| 6,383,550 B1 | 5/2002 | Juillerat et al. |
| 6,528,099 B1 | 3/2003 | Garti et al. |
| 6,861,083 B2 | 3/2005 | Martel et al. |
| 7,000,534 B1 | 2/2006 | Mendes |
| 7,033,623 B2 | 4/2006 | Suzuki et al. |
| 7,175,863 B1 | 2/2007 | Mathias et al. |
| 8,178,148 B2 | 5/2012 | Fujii et al. |
| 8,486,470 B2 | 7/2013 | Laukli et al. |
| 8,784,914 B2 | 7/2014 | Leloup et al. |
| 8,840,948 B2 | 9/2014 | Yamamoto et al. |
| 8,980,362 B2 | 3/2015 | Du et al. |
| 9,084,436 B2 | 7/2015 | Sorensen et al. |
| 9,243,843 B2 | 1/2016 | Savarese |
| 9,422,504 B2 | 8/2016 | Msika et al. |
| 9,526,270 B2 | 12/2016 | Balder |
| 9,862,666 B2 | 1/2018 | Soum et al. |
| 9,862,911 B2 | 1/2018 | Acuna Llanes |

(Continued)

FOREIGN PATENT DOCUMENTS

| | | |
|---|---|---|
| GB | 1203284 A | 8/1970 |
| WO | 87/03951 A1 | 7/1987 |

(Continued)

OTHER PUBLICATIONS

International Search Report (PCT/US16/49942); dated Oct. 21, 2016.
International Preliminary Report on Patentability (PCT/US2016/049942); dated Mar. 6, 2018.
Stalmach, A et al., Metabolite Profiling of Hydroxycinnamate Derivatives in Plasma and Urine after the Ingestion of Coffee by Humans: Identification of Biomarkers of Coffee Consumption., Drug Metabolism and Disposition, vol. 37, No. 8, 2009, pp. 1749-1758; abstract; p. 1749, col. 1, paragraph 1; p. 1752, col. 2, paragraph 7; p. 1753, col. 1, paragraph 4.
Fresco, P. et al., New Insights on the Anticancer Properties of Dietary Polyphenois, Medicinal Research Reviews, vol. 26, No. 6, 2006, pp. 747-766; p. 750, table 1.

(Continued)

*Primary Examiner* — Anthony J Weier
(74) *Attorney, Agent, or Firm* — Howard & Howard Attorneys PLLC

(57) ABSTRACT

The present invention provides methods for preparing antioxidant-rich products from coffee cherries for nutritional and cosmetic uses. In one aspect, the present invention provides a method for preparing a liquid coffee fruit extract and a liquid coffee fruit extract prepared by the method. In another aspect, the present invention provides a method for preparing dried coffee fruit and a dried coffee fruit product prepared by the method. In yet another aspect, the present invention provides a method for preparing a coffee fruit powder and a coffee fruit powder prepared by the method. The coffee fruit products prepared by the methods of the present invention contain high levels of powerful antioxidants capable of reducing oxidation and preventing oxidative damage for the prevention or treatment of a vast array of diseases and conditions.

26 Claims, No Drawings

(56) References Cited

U.S. PATENT DOCUMENTS

| | | | |
|---|---|---|---|
| 9,879,284 B2 | 1/2018 | Gonzalez Marin et al. | |
| 2002/0187239 A1* | 12/2002 | Miljkovic | A23F 5/02 426/590 |
| 2004/0037938 A1 | 2/2004 | Smith | |
| 2006/0263507 A1 | 11/2006 | Miljkovic et al. | |
| 2006/0263508 A1 | 11/2006 | Miljkovic et al. | |
| 2007/0281048 A1 | 12/2007 | Miljkovic | |
| 2009/0104310 A1* | 4/2009 | Nakajima | A23F 5/02 426/45 |
| 2009/0175973 A1* | 7/2009 | Vikhrieva | A61K 31/375 424/777 |
| 2014/0370181 A1 | 12/2014 | Young et al. | |
| 2015/0017270 A1 | 1/2015 | Velez et al. | |
| 2015/0119408 A1 | 4/2015 | Fields | |
| 2016/0021894 A1* | 1/2016 | Belliveau | A21D 13/047 426/296 |
| 2016/0030350 A1 | 2/2016 | Muller | |
| 2016/0165934 A1* | 6/2016 | Hirschberg | A23L 19/07 426/615 |
| 2018/0235251 A1 | 8/2018 | Muller | |
| 2018/0289030 A1 | 10/2018 | Muller | |

FOREIGN PATENT DOCUMENTS

| | | |
|---|---|---|
| WO | 02/062159 A1 | 8/2002 |
| WO | 2014/143328 A1 | 9/2014 |
| WO | 2014/158267 A1 | 10/2014 |
| WO | 2015/013199 A1 | 1/2015 |
| WO | 2015/078594 A1 | 6/2015 |

OTHER PUBLICATIONS

Zhang, Qing-Wen et al., Techniques for extraction and isolation of natural products: a comprehensive review, Chinese Medicine, 2018, 26 pages, Springer Nature.

Bucar, Franz et al., Natural product isolation—how to get from biological material to pure compounds, Nat. Prod. Rep., 2013, 30, 525-545, RSC Publishing.

Clifford et al. (1991) "Phenols and caffeine in wet-processed coffee beans and coffee pulp", Food Chemistry, 40(1): 35-42.

Clifford (1986) "Coffee bean dicaffeoylquinic acids", Phytochemistry, 25(7): 1767-1769.

Baiq Rien Handayani (2009) "Study and characterization of antibacterial compounds of Arabica coffee berry pulp" PhD Thesis.

A.A.Abd El-Moneim et al. (2015) "Effect of Honey and Citric Acid Treatments on Postharvest Quality of Fruits and Fresh-Cut of Guava", World J. Agric. Sci., 11(5): 255-267.

Baldwin EA (2007) "Surface Treatments and Edible Coatings in Food Preservation" Handbook of Food Preservation, Second Edition (Rahman MS, Ed.).

Rathinavelu et al. (2005) "Potential alternative use of coffee wastes and by-products" Use of coffee wastes and by-products: A summary.

Baldwin et al. (1996) "Improving storage life of cut apple and potato with edible coating", Postharvest Biology and Technology, 9: 151-163.

Santerre et al. (1988) "Ascorbic Acid/Citric Acid Combinations in the Processing of Frozen Apple Slices" J. Food Sci., 53(6): 1713-1716.

Jahanban-Esfahlan, et al., A Comparative Review on the Extraction, Antioxidant Content and Antioxidant Potential of Different Parts of Walnut (*Juglans regia* L.) Fruit and Tree, Molecules 20199, 24, 2133, doi:10.3390/molecules2411213 (www/mdpi.com/journal/molecules).

Terefe, et al., Texture and Microstructure, Chapter IV, CSIRO Food and Science and Nutrition, 56 pages, 671 Sneydes Road, Werribee, VIC 3030, Australia.

* cited by examiner

PREPARATION OF COFFEE FRUIT EXTRACTS AND POWDERS

CROSS-REFERENCE TO RELATED APPLICATION

The present application is a U.S. National Stage of International Patent Application No. PCT/US2016/049942, filed on Sep. 1, 2016, and which claims priority to U.S. Provisional Application No. 62/214,723, filed Sep. 4, 2015, both disclosures of which are hereby incorporated by reference in their entirety for all purposes.

TECHNICAL FIELD

The present invention relates generally to processes for isolating and extracting antioxidants and other beneficial compounds from coffee cherries and antioxidant-rich products and compositions made from coffee cherries.

BACKGROUND OF THE INVENTION

The fruit of the coffee plant (e.g., *Coffea arabica*) is often called the "coffee cherry." The coffee cherry is made up of the following layers (from the outside in): skin, pulp, mucilage, parchment, and bean. The skin, also referred to as the epicarp or exocarp, is a monocellular layer covered with a waxy substance ensuring protection of the fruit. The mesocarp includes the pulp and the mucilage. The pulp is the fleshy outer layer of the mesocarp, directly beneath the skin, which during processing can be removed with a pulping machine. The mucilage is the slimy layer found between the pulp and parchment, adhering to the parchment inside a coffee cherry. It is generally not removed by pulping. Mucilage is not present in unripe coffee fruit, and disappears in overripe coffee. The endocarp, or "parchment," is the tough integument tightly pressed to the bean when fresh but from which the bean shrinks during drying. It lies between the fleshy part (or pulp) of the cherry and the silver skin. The endocarp also includes the thin, crumbly paper-like covering that is left on wet-processed coffee beans after pulping and fermentation, and which is subsequently removed during hulling. The bean includes the endosperm and the embryo. The endosperm includes the tissues that feed the embryo during germination. The embryo ultimately forms the coffee beans. The silver skin is the seminal integument covering the endosperm, i.e., the thin, papery, shiny layer immediately surrounding the coffee bean, being the remnant of the integument. During processing, milling before export removes most silver skin, and the remainder is removed during roasting in the form of chaff. The endosperm fills the integument as the coffee cherry ripens.

The coffee cherry is harvested and processed to make coffee. During processing, the bean portion of the cherry is removed and further processed using various techniques. This processing generally removes the bean, silver skin and parchment. Thus, after the bean is removed, a significant amount of the coffee cherry fruit remains.

Traditionally, the portion of the cherry remaining after the bean is removed is viewed as waste, although it is sometimes processed into compost or animal feed. However, this remaining portion has significant nutritive value. In particular, it is high in antioxidants and polyphenols, including chlorogenic acids of various types, caffeic acid, quinic acid, ferulic acid, proanthocyanidins, and others. These compounds have antioxidant activity, which can contribute to good heath by reducing oxidative injury and thus ameliorating associated disease states such as diabetes, Alzheimer's disease, and certain types of cardiovascular and neurological conditions. The beneficial anti-oxidative and other properties of such compounds, as well as other beneficial components of the extracts, can also be used to treat other conditions such as skin disorders and the like. Isolating these antioxidants and other beneficial compounds from the de-beaned coffee cherry can be difficult, however. For example, coffee pulp contains high levels of tannins, which bind the protein and make it difficult to extract and precipitate. An additional problem is that the free phenols in coffee pulp become oxidized to quinones. Quinones are oxidizing agents that may oxidize amino acids in coffee cherry proteins. Also, ripe coffee fruit is used during husking, and exposure to oxygen, and also the activity of enzymes, sugars, and other components of the coffee cherries, can cause rapid degradation and/or oxidation of these compounds and rapid bacterial growth either prior to or during processing. These degradative processes can begin almost immediately following removal of the bean. As a result, currently available methods of isolating the beneficial components from coffee cherries have frequently resulted in poor yields and the presence of undesirable side-products.

As such, there remains a need in the art for improved methods of isolating antioxidants and other beneficial compounds from coffee cherries and antioxidant-rich products and compositions made from coffee cherries. The present invention satisfies these needs and provides related advantages as well.

BRIEF SUMMARY OF THE INVENTION

In some aspects, the present invention provides a method for preparing a liquid coffee fruit extract and a liquid coffee fruit extract prepared by the method. In particular embodiments, the method comprises: (a) providing de-beaned coffee cherries; (b) freezing the de-beaned coffee cherries under substantially oxygen-free conditions at a temperature of less than about −30° Fahrenheit (F) to produce frozen de-beaned coffee cherries; (c) thawing the frozen de-beaned coffee cherries to produce thawed de-beaned coffee cherries; and (d) extracting antioxidants from the thawed de-beaned coffee cherries in a heated aqueous solvent to produce a liquid coffee fruit extract and extracted de-beaned coffee cherries.

In other aspects, the present invention provides a method for preparing a dried coffee fruit product and a dried coffee fruit product prepared by the method. In particular embodiments, the method comprises: (a) providing de-beaned coffee cherries; (b) dehydrating the de-beaned coffee cherries to produce partially dried de-beaned coffee cherries having a moisture level of from about 10% to about 15%; and (c) dehydrating the partially dried de-beaned coffee cherries to produce a dried coffee fruit product having a moisture level of from about 2% to about 4%.

In certain embodiments, the present invention provides a coffee fruit powder prepared by grinding the dried coffee fruit product. In other embodiments, the present invention provides a coffee fruit powder prepared by drying (e.g., pulse drying) the coffee fruit extract. In yet other embodiments, the present invention provides a fortified or enriched coffee fruit powder prepared by spraying the dried coffee fruit product with the coffee fruit extract prior to grinding.

In yet other aspects, the present invention provides a coffee fruit extract comprising a total phenolic acid concentration of at least about 5% (w/w). In some instances, the coffee fruit extract comprises a total phenolic acid concentration of at least about 20% (w/w). In certain instances, the coffee fruit extract has a Brix value of about 40. In other instances, the phenolic acids present in the coffee fruit extract include, but are not limited to, chlorogenic acid, caffeic acid, ferulic acid, isoferulic acid, dihydroferulic acid, quinic acid, and combinations thereof.

In further aspects, the present invention provides a coffee fruit powder comprising a total phenolic acid concentration of from about 7% and about 12% (w/w). In certain instances, the phenolic acids present in the coffee fruit powder include, but are not limited to, chlorogenic acid, caffeic acid, ferulic acid, isoferulic acid, dihydroferulic acid, quinic acid, and combinations thereof.

The methods and compositions described herein may be implemented in any means for achieving various aspects. Other features of the present embodiments will be apparent from the detailed description that follows.

BRIEF DESCRIPTION OF THE DRAWINGS

None

DETAILED DESCRIPTION OF THE INVENTION

I. Introduction

Human cells create "life energy" through oxidation processes; however, excessive oxidation can also cause cell damage. The human body has various systems of controlling oxidation in our cells by using antioxidants. However, because of factors resulting from our highly industrialized society-including pollution, radiation, stress, and our busy lifestyles-our bodies cannot eliminate oxidation as fast as it accumulates, causing a vast range of health issues. Reducing oxidation and the oxidation damage from the human body is one of the most important issues for human health. Creating a supply of antioxidant large enough to supply humans on a global scale has been the greatest issue as antioxidant-rich materials are difficult to source and expensive to process.

Coffee is the world's second largest agricultural crop, but only a small percentage of its fruit, the bean, is used. Using the present invention, the "by-product" of coffee production, which has previously been viewed as waste, can provide a valuable source of the powerful antioxidants and other beneficial compounds contained in the fruit to make them more readily and abundantly available to the general public.

In certain aspects, the present invention provides methods for preparing a liquid coffee fruit extract where de-beaned coffee cherries containing skin, pulp, and mucilage are frozen under substantially oxygen-free conditions at a temperature of less than about −30° F. and then thawed prior to and during the extraction step in a heated aqueous solvent such as hot water. Without being bound by any particular theory, the large change in temperature when the de-beaned coffee cherries are added to the heated aqueous solvent causes the cells of the coffee fruit to "burst," releasing antioxidants, nutrients, and other compounds from inside the cells. The resulting liquid coffee fruit extract is advantageously highly concentrated with antioxidants including polyphenols as well as nutrients and other compounds (e.g., has a Brix value of about 40), and typically has a minimum of about 5% (w/w) (e.g., at least about 20% (w/w)) total phenolic acids including chlorogenic acid, caffeic acid, ferulic acid, isoferulic acid, dihydroferulic acid, and quinic acid. The liquid coffee fruit extract has beneficial anti-oxidative and anti-inflammatory properties.

In certain other aspects, the present invention provides methods for preparing a dried coffee fruit product where de-beaned coffee cherries containing skin, pulp, and mucilage are dehydrated in two steps that initially brings the moisture level of the de-beaned coffee cherries to about 10% to about 15% and then brings the moisture level down to about 2% to about 4%. In certain embodiments, the dried coffee fruit product can be sprayed with a liquid coffee fruit extract described herein to fortify the dried coffee fruit product by enriching it antioxidants including polyphenols as well as nutrients and other compounds present in the concentrated liquid extract. The unfortified or fortified dried coffee fruit product can be ground into a coffee fruit powder. The resulting coffee fruit powder is advantageously highly concentrated with antioxidants including polyphenols as well as nutrients and other compounds, and typically has from about 7% and about 12% (w/w) total phenolic acids including chlorogenic acid, caffeic acid, ferulic acid, isoferulic acid, dihydroferulic acid, and quinic acid. The dried coffee fruit and powder products have beneficial anti-oxidative and anti-inflammatory properties.

II. Description of the Embodiments

The methods described herein can be used to produce antioxidant-rich products including liquid coffee fruit extracts, dried coffee fruits, and coffee fruit powders.

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention.

The terms "a," "an," or "the" as used herein include plural referents unless the context clearly dictates otherwise.

The terms "about" and "around," as used herein to modify a numerical value, indicate a close range surrounding that explicit value. If "X" were the value, "about X" or "around X" would indicate a value from 0.8 X to 1.2 X, preferably a value from 0.9 X to 1.1 X, and, more preferably, a value from 0.95 X to 1.05 X. Any reference to "about X" or "around X" specifically indicates at least the values X, 0.95 X, 0.96 X, 0.97 X, 0.98 X, 0.99 X, 1.01 X, 1.02 X, 1.03 X, 1.04 X, and 1.05 X. Thus, "about X" and "around X" are intended to teach and provide written description support for a claim limitation of, e.g., "0.98 X."

In some aspects, the present invention provides a method for preparing a liquid coffee fruit extract and a liquid coffee fruit extract prepared by the method. In particular embodiments, the method comprises: (a) providing de-beaned coffee cherries; (b) freezing the de-beaned coffee cherries under substantially oxygen-free conditions at a temperature of less than about −30° F. to produce frozen de-beaned coffee cherries; (c) thawing the frozen de-beaned coffee cherries to produce thawed de-beaned coffee cherries; and (d) extracting antioxidants from the thawed de-beaned coffee cherries in a heated aqueous solvent to produce a liquid coffee fruit extract and extracted de-beaned coffee cherries.

In some embodiments, the de-beaned coffee cherries consist of skin, pulp, and mucilage. In certain embodiments, the de-beaned coffee cherries are harvested from unripe coffee cherries, nearly ripe coffee cherries, ripe coffee cherries, or mixtures thereof. In preferred embodiments, the de-beaned coffee cherries are harvested from ripe coffee cherries. In other embodiments, the antioxidants comprise one or more phenolic acids, proanthocyanidins, other phytochemicals (e.g., flavonoids) and/or nutrients (e.g., prodelphinidins, procyanidins, trigonelline, lignins, tannins such as condensed tannins, coffee saccharides, anthocyanins, vitamins, and the like), or combinations thereof. Non-limiting examples of phenolic acids include chlorogenic acid, caffeic acid, ferulic acid, isoferulic acid, dihydroferulic acid, quinic acid, and combinations thereof.

In some embodiments, the method further comprises promptly contacting the de-beaned coffee cherries with a coating comprising ascorbic acid and citric acid to produce coated de-beaned coffee cherries prior to freezing them. In certain instances, the de-beaned coffee cherries are frozen at a temperature of about −30° F. In other instances, the frozen de-beaned coffee cherries are thawed (e.g., partially or completely thawed) at a temperature of about 30° F.

In some embodiments, the antioxidants are extracted by mixing, agitating, and/or macerating the thawed de-beaned coffee cherries in the heated aqueous solvent. In certain instances, the heated aqueous solvent comprises purified water. In other instances, the purified water is heated to a temperature of about 180° F.

In some embodiments, the method further comprises pressing the extracted de-beaned coffee cherries with the coffee fruit extract to produce a pressed coffee fruit extract. In other embodiments, the method further comprises filtering the pressed coffee fruit extract to produce a filtered coffee fruit extract. In certain instances, the filtered coffee fruit extract has a Brix value of between about 3.5 to about 15 (e.g., a Brix value of up to about 14).

In some embodiments, the method further comprises separating and removing any sediment or pulp from the filtered coffee fruit extract. In other embodiments, the method further comprises concentrating the filtered coffee fruit extract to produce a concentrated coffee fruit extract. In certain instances, the filtered coffee fruit extract is concentrated using a vacuum evaporator at a temperature of less than about 100° F.

In some embodiments, the method further comprises separating and removing any sediment when the concentrated coffee fruit extract reaches a Brix value of about 20. In other embodiments, the concentrated coffee fruit extract is further concentrated to a Brix value of about 40 to produce the coffee fruit extract. In particular embodiments, the coffee fruit extract has a total phenolic acid concentration of at least about 5% (w/w). In some instances, the coffee fruit extract comprises a total phenolic acid concentration of at least about 20% (w/w). In certain instances, the total phenolic acid concentration comprises a mixture of chlorogenic acid, caffeic acid, ferulic acid, isoferulic acid, dihydroferulic acid, and quinic acid. In some instances, the coffee fruit extract promotes cell growth and cell viability. In other instances, the coffee fruit extract inhibits NFκB expression in human cells. The coffee fruit extract has beneficial anti-oxidative and anti-inflammatory properties.

In other aspects, the present invention provides a method for preparing a dried coffee fruit product and a dried coffee fruit product prepared by the method. In particular embodiments, the method comprises: (a) providing de-beaned coffee cherries; (b) dehydrating the de-beaned coffee cherries to produce partially dried de-beaned coffee cherries having a moisture level of from about 10% to about 15%; and (c) dehydrating the partially dried de-beaned coffee cherries to produce a dried coffee fruit product having a moisture level of from about 2% to about 4%.

In some embodiments, the de-beaned coffee cherries consist of skin, pulp, and mucilage. In certain embodiments, the de-beaned coffee cherries are harvested from unripe coffee cherries, nearly ripe coffee cherries, ripe coffee cherries, or mixtures thereof. In preferred embodiments, the de-beaned coffee cherries are harvested from ripe coffee cherries. In other embodiments, the dried coffee fruit product comprises antioxidants. In certain instances, the antioxidants comprise one or more phenolic acids, proanthocyanidins, other phytochemicals (e.g., flavonoids) and/or nutrients (e.g., prodelphinidins, procyanidins, trigonelline, lignins, tannins such as condensed tannins, coffee saccharides, anthocyanins, vitamins, and the like), or combinations thereof. Non-limiting examples of phenolic acids include chlorogenic acid, caffeic acid, ferulic acid, isoferulic acid, dihydroferulic acid, quinic acid, and combinations thereof.

In some embodiments, the method further comprises promptly contacting the de-beaned coffee cherries with a coating comprising ascorbic acid and citric acid to produce coated de-beaned coffee cherries prior to dehydrating them.

In some embodiments, the method further comprises freezing the de-beaned coffee cherries under substantially oxygen-free conditions at a temperature of less than about −30° F. to produce frozen de-beaned coffee cherries prior to dehydrating them. In certain instances, the de-beaned coffee cherries are frozen at a temperature of about −30° F.

In some embodiments, the method further comprises thawing the frozen de-beaned coffee cherries to produce thawed de-beaned coffee cherries prior to dehydrating them. In certain instances, the frozen de-beaned coffee cherries are thawed (e.g., partially or completely thawed) at a temperature of about 30° F. In other instances, the de-beaned coffee cherries are shredded prior to dehydrating them.

In some embodiments, the de-beaned coffee cherries have an initial moisture level of from about 85% to about 90% prior to dehydrating them. In certain embodiments, the de-beaned coffee cherries are partially dried using a cold dehydrator at a temperature of less than about 125° F. In certain instances, the de-beaned coffee cherries are partially dried using a stainless steel mesh belt dryer or a heated air cyclone. In other embodiments, the partially dried de-beaned coffee cherries are dried using a finish dryer.

In some embodiments, the method further comprises contacting (e.g., spraying) the dried coffee fruit product with a coffee fruit extract to fortify the dried coffee fruit product. In other embodiments, the method further comprises grinding the dried coffee fruit product to produce a coffee fruit powder. In particular embodiments, the coffee fruit powder comprises a total phenolic acid concentration of from about 7% and about 12% (w/w). In certain instances, the total phenolic acid concentration comprises a mixture of chlorogenic acid, caffeic acid, ferulic acid, isoferulic acid, dihydroferulic acid, and quinic acid.

In certain embodiments, the dried coffee fruit or coffee fruit powder promotes cell growth and cell viability. In certain other embodiments, the dried coffee fruit or coffee fruit powder inhibits NFκB expression in human cells. The dried coffee fruit or coffee fruit powder has beneficial anti-oxidative and anti-inflammatory properties.

In yet other aspects, the present invention provides a method for preparing a concentrated coffee fruit powder comprising drying a coffee fruit extract prepared by the method described herein. In certain embodiments, the coffee fruit extract is subjected to pulse drying to produce the concentrated powder. In particular embodiments, the concentrated powder contains high levels of antioxidants including one or more phenolic acids. The concentrated powder has beneficial anti-oxidative and anti-inflammatory properties.

In certain embodiments, the present invention provides a coffee fruit powder prepared by grinding the dried coffee fruit product. In other embodiments, the present invention provides a concentrated coffee fruit powder prepared by drying the coffee fruit extract. In yet other embodiments, the present invention provides a fortified or enriched coffee fruit powder prepared by contacting (e.g., spraying) the dried coffee fruit product with the coffee fruit extract prior to grinding.

In further aspects, the present invention provides a coffee fruit extract comprising a total phenolic acid concentration of at least about 5% (w/w). In some instances, the coffee fruit extract comprises a total phenolic acid concentration of at least about 20% (w/w). In certain instances, the coffee fruit extract has a Brix value of about 40. In other instances, the phenolic acids present in the coffee fruit extract include, but are not limited to, chlorogenic acid, caffeic acid, ferulic acid, isoferulic acid, dihydroferulic acid, quinic acid, and combinations thereof.

In related aspects, the present invention provides a coffee fruit powder comprising a total phenolic acid concentration of from about 7% and about 12% (w/w). In some instances, the phenolic acids present in the coffee fruit powder include, but are not limited to, chlorogenic acid, caffeic acid, ferulic acid, isoferulic acid, dihydroferulic acid, quinic acid, and combinations thereof.

III. Selection of Coffee Cherries and Preparation for Further Processing

The coffee cherries can be at any stage of ripeness that is consistent with the presence of antioxidants, nutrients, and other beneficial compounds from the coffee cherries. The stage of ripeness is generally reflected by the amount of green coloring that remains on the surface of the coffee cherries, with more green coloring indicating increasingly less ripeness. The coffee cherries for use in the methods described herein can be green over, for example, about 50%, about 40%, about 30%, about 20%, about 10%, about 5%, or about 1% of their surface, or the coffee cherries can be ripe, that is, red in color. In exemplary embodiments, the coffee cherries are ripe or nearly ripe (e.g., less than about 10% or less than about 5% green on their surface).

The coffee cherries can, for example, be de-beaned prior to further processing, or the entire (whole) coffee cherry can be employed. In exemplary embodiments, the coffee cherries are de-beaned. However, wherever "de-beaned coffee cherries" is used herein, a person of ordinary skill in the art would understand that entire coffee cherries can be substituted. Thus, the present invention is particularly applicable to the use of ripe cherries used in a coffee production process after the de-beaning. These cherries are generally viewed as waste from the production process owing to their rapid degradation. The de-beaned coffee cherries used in the methods described herein typically contain skin, pulp, and mucilage. As used herein, unless the context indicates otherwise, "skins," when used in reference to coffee fruit, can be understood as equivalent to "de-beaned coffee cherries."

Providing De-Beaned Coffee Cherries

De-beaned coffee cherries for use in the methods of the present invention can be provided using any method known in the art, such as the methods described herein. In exemplary embodiments, whole coffee cherries are received, washed, and floated in water to eliminate "floaters." Undesirable cherries, including overripe or underdeveloped cherries float. Selected cherries are then "de-beaned" (pulped) using a coffee pulping machine which separates the coffee bean and coffee fruit. De-beaned coffee cherries, which can also be referred to herein as coffee fruit or skins containing pulp and mucilage, can optionally be sprayed with a preservative coating via an electric or hand operated sprayer attached to the pulping machine. The de-beaned coffee cherries can travel through a liquid medium (water) to the coffee fruit collection point, at which point the coffee fruit can be put into a press/extruder to remove the excess water on the skins that accumulated from transport. Alternatively, a vibrational screen or centrifuge can also be used to remove the water.

Optional Preservative Coating

The optional preservative coating can be applied to the de-beaned coffee cherries promptly after de-beaning. The optional preservative coating can have the effect of inhibiting the degradation of the antioxidants and other beneficial compounds in the coffee fruit, for example, by preventing oxidation or enzymatic degradation. For example, phenolic compounds in the coffee fruit can be oxidized by an enzyme called polyphenol oxidase (PPO). This process is evidenced by the browning of the coffee fruit. Also, coffee fruit enzymes can convert free phenols and amino acids to quinic acid. The coating retards these degradative processes and denatures the enzymes that promote oxidation, thus preserving higher amounts of antioxidants, amino acids, and free phenols.

As used herein, "promptly" means within a period of time that is consistent with preservation of all or a substantial portion of the antioxidants and other beneficial compounds in the coffee cherry. "Promptly" can mean, for example, within about 24 hours, within about 12 hours, within about 6 hours, within about 4 hours, within about 3 hours, within about 2 hours, within about 1 hour, within about 45 minutes, within about 30 minutes, within about 15 minutes, within about 5 minutes, within about 1 minute, within about 30 seconds, within about 15 seconds, within about 10 seconds, or within about 5 seconds or less after the previous step in the process, or after the event referenced, as applicable. For example, the coating can be applied within about 5 minutes, or within about 1 minute, or within about 30 seconds after de-beaning.

The optional coating can include, for example, one or more of ascorbic acid, citric acid, acetic acid, benzoic acid, sulfur dioxide, sulfites such as potassium sulfite or combinations of two or more of these compounds. For example, the coating can include a combination of ascorbic acid and citric acid in water or another suitable solvent.

The ascorbic acid can be used in an amount of up to or about 1 gram per gallon, 2 grams per gallon, 3 grams per gallon, 4 grams per gallon, 5 grams per gallon, 6 grams per gallon, 7 grams per gallon, 8 grams per gallon, 9 grams per gallon, 10 grams per gallon, 11 grams per gallon, 12 grams per gallon, 13 grams per gallon; 14 grams per gallon, 15 grams per gallon, 20 grams per gallon of water or suitable solvent or more, or about 10-30, about 10-20, or about 12-16 grams per gallon. In some embodiments, powder such as a food-grade powder of ascorbic acid can be used. For example, the ascorbic acid can be present in about 15 grams food grade powder per gallon of water or other suitable solvent.

The citric acid can be used in an amount of up to or about 0.5 grams per gallon, 1 gram per gallon, 2 grams per gallon, 3 grams per gallon, 4 grams per gallon, 5 grams per gallon, 6 grams per gallon, 7 grams per gallon, 8 grams per gallon, 9 grams per gallon, 10 grams per gallon, 11 grams per gallon, 12 grams per gallon, 13 grams per gallon, 14 grams per gallon, 15 grams per gallon, 20 grams per gallon or more, or about 1-15, 2-10, or 5-10 grams per gallon. In some embodiments, powder such as a food-grade powder of citric acid can be used.

The ratio of ascorbic acid to citric acid can be from about 4:1 to about 1:4. In exemplary embodiments, the ratio of ascorbic acid to citric acid can be about 4:1 to about 1:2, about 3:1 to about 1:1 or about 2:1. For example, the coating can be made up of about 15 grams of ascorbic acid and 7 grams of citric acid per gallon of water. One gallon of the coating can be used to treat about 100-200, about 125-175, or about 150 pounds of de-beaned coffee cherries.

Optional Storage of Coffee Cherries Before Processing

Depending on the circumstances under which the process is being performed, it may be desirable to store the de-beaned coffee cherries before they are further processed. In such circumstances, the storage can be done under substantially oxygen-free and/or refrigerated conditions. As used herein, "substantially oxygen-free conditions" and "oxygen-free conditions" are used interchangeably and mean conditions under which the de-beaned coffee cherries or processed components thereof are protected against exposure to oxygen in such quantities or activities as to favor the oxidative and/or enzymatic degradation of the antioxidants and/or other beneficial compounds in the de-beaned coffee cherries. Any level of oxygen that fails to produce substantial oxidative and/or enzymatic degradation of antioxidants and/or beneficial compounds is encompassed within "oxygen-free conditions." Oxygen-free conditions can be achieved, for example, by removing most or all oxygen from the environment around the coffee cherries, for example by evacuating and sealing a container holding the coffee cherries, or by replacing oxygen with a different gas, including an inert gas such as nitrogen, argon, carbon dioxide, or combinations thereof. Other means of achieving oxygen-free conditions can also be utilized, for example by immersing the coffee cherries in a fluid with little or no oxygen or oxidative activity, such as a citric acid/ascorbic acid mixture disclosed herein, or lemon juice, sodium metabisulfate solution or sulfur dioxide, or by rendering ineffective or inactive the oxygen that is present in the environment. For example, oxygen-free conditions can be achieved by placing the coffee cherries in one or more containers and evacuating the containers. The containers can be any suitable airtight unit designed for storage, including food-grade poly bags, containment drums with or without liners, trash cans with or without liners, and/or trash/lawn/freezer bags, and can be of any capacity, for example, of about 50 lb. capacity. Any step in the methods described herein can be suitable for performing under oxygen-free conditions.

If the de-beaned coffee cherries are to be stored under oxygen-free conditions, the coffee cherries are generally subjected to such conditions promptly after the cherries are de-beaned, for example, within about one minute after de-beaning. For example, the de-beaned coffee cherries can be transported for about 1 minute before being bagged, vacuumed, and sealed. In other embodiments, the de-beaned coffee cherries are stored under oxygen-free conditions after about 2, 3, 4, 5, or more minutes.

Whether or not stored under oxygen-free conditions, the de-beaned coffee cherries can also be stored under refrigerated conditions. As used herein, the term "refrigerated conditions" means any conditions of temperature that are effective to inhibit oxidative and/or enzymatic degradation of the antioxidants and other beneficial compounds in coffee cherries. Thus, refrigeration represents one readily and economically achievable method of reducing or eliminating the activity and detrimental effect of any oxygen or residual oxygen in the environment. Refrigerated conditions may also serve to promote cell lysis in the coffee cherries, which promote release of beneficial compounds from the cells, facilitating further processing. Such conditions may also serve to denature enzymes that contribute to degradation of the coffee cherries. For example, the term "refrigerated conditions" encompasses temperatures lower than or at about 60° F., about 50° F., about 40° F., about 35° F., about 32° F., about 30° F., about 20° F., about 10° F., about 0° F., about −10° F., about −20° F., about −30° F., about −40° F., about −50° F., about −60° F., about −70° F., about −80° F., about −90° F., about −100° F., or lower. Temperatures below about 32° F. can also be considered freezing conditions. As such, the term "freezing conditions" is encompassed within the term "refrigerated conditions." For example, the de-beaned coffee cherries can be stored under freezing conditions. If the de-beaned coffee cherries are to be stored under refrigerated conditions, they are subjected to such conditions promptly after the cherries are de-beaned, for example within about 15 minutes, about 5 minutes, or about 2 minutes after de-beaning. In exemplary embodiments, removal of oxygen and refrigeration (e.g., freezing) is performed promptly following de-beaning.

De-beaned coffee cherries that are subjected to storage under oxygen-free and/or refrigerated conditions can be stored under such conditions for any length of time that is consistent with preservation of at least a substantial portion of the antioxidants and/or other beneficial compounds in the coffee cherries. Such storage can last, for example, up to about 2 hours, about 4 hours, about 6 hours, about 12 hours, about 24 hours, about 3 days, about one week, about 2 weeks, about one month, about 2 months, about 3 months, about 4 months, about 5 months, about 6 months, about 12 months, about 18 months, about 24 months, or longer. For example, such storage can last up to about 6 months, though frozen de-beaned coffee cherries that have reached the time limit can be processed and preserved as dried skins. Should transport be desirable in order to deliver the coffee cherries to a storage facility, such transport can also take place under oxygen-free and/or refrigerated conditions.

IV. Process for Preparing Coffee Fruit Extract

In one aspect, the present invention provides a process for preparing a liquid extract that is rich in antioxidants and other beneficial compounds from de-beaned coffee cherries. In this process, coffee cherries are selected, de-beaned, optionally sprayed with a preservative coating, and frozen under refrigerated conditions as described herein. In exemplary embodiments, the de-beaned coffee cherries are frozen at a temperature of less than about −30° F. in a container such as a deoxygenated food-safe poly bag. In alternative embodiments, the de-beaned coffee cherries are frozen at a temperature of less than about −30° F. in a container such as a food-safe poly bag without deoxygenating. In particular embodiments, de-beaned coffee cherries are frozen for a suitable period of time (e.g., about 24 hours) before they are partially or completely thawed for the extraction step. In alternative embodiments, frozen coffee cherries are promptly contacted with an aqueous solvent (e.g., at an elevated temperature) for the extraction step.

Extracting Coffee Fruit Nutrients

Extraction of the coffee fruit nutrients can be achieved by using any means known in the art that is suitable for extracting the antioxidants and/or other beneficial compounds in coffee cherries. For example, the de-beaned coffee cherries can be contacted with an aqueous solvent such as water in an extraction tank. Other suitable solvents include methanol, ethanol, or a combination of either or both of methanol and ethanol with water. For example, the aqueous solvent can be about a 50/50 (measured by volume, by weight, or by w/v or v/w) mixture of water and ethanol, or water and methanol. In particular embodiments, the aqueous solvent is water. The water can be purified water, and such purification can be carried out by any known method, including for example reverse osmosis, membrane filtering, charcoal bed filtering, deionization, distillation or a combination of these methods. For example, the aqueous solvent can be lab-quality water, prepared by subjecting it to reverse osmosis and then de-ionizing it. For example, the water can be prepared by subjecting it to reverse osmosis, membrane filtering, and charcoal bed filtering to reach a high level of purity, e.g., <3 ppm, and then de-ionizing. The water or other extraction fluid can optionally contain additional preservatives such as ascorbic acid, citric acid, or others known in the art. The extraction can also be done using ultra-high pressure extraction (known as UPE), which can be useful for extracting phenols or other antioxidants or beneficial compounds in coffee cherries. In UPE, high pressure can be used to "push" the solvent through the material without excessive heat that could cause degradation.

The temperature of the aqueous solvent can be an elevated temperature, for example, above room temperature. The temperature of the aqueous solvent can be, for example, at least about 70° F., 80° F., 90° F., 100° F., 110° F., 120° F., 130° F., 140° F., 145° F., 150° F., 155° F., 160° F., 170° F., 180° F., 190° F., 200° F., 210° F., or higher. The amount of the aqueous solvent used in the extraction can be expressed as a ratio versus the amount of de-beaned coffee cherries. For example, the aqueous solvent:coffee fruit ratio (in units of gallons solvent:pounds coffee fruit) can be at least about 0.01:1, 0.1:1, 0.2:1, 0.3:1, 0.4:1, 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2:1, or higher. The extraction can be carried out under oxygen-free conditions.

In certain embodiments, extraction is achieved by adding frozen or partially or completely thawed de-beaned coffee cherries to a heated aqueous solvent such as hot filtered water (about 180° F.). Without being bound by any particular theory, the temperature difference between the coffee cherries and the hot water causes the cells to burst or lyse, releasing the nutrients (e.g., antioxidants and/or other beneficial compounds) within the cells. In particular embodiments, de-beaned coffee cherries frozen at −30° F. are first slowly warmed from −30° F. to +30° F. in a controlled temperature room in a process that takes from about 8-16 hours (approximately overnight) before adding the (partially) thawed coffee cherries to a heated aqueous solvent such as hot water (about 180° F.) to perform the extraction of antioxidants and/or other beneficial compounds. The extraction steps described herein can be performed once, or they can be performed multiple times, in order to achieve desired purity and yield.

In some embodiments, de-beaned coffee cherries to be extracted can optionally be subjected to a maceration step. During the maceration step, the de-beaned coffee cherries are chopped into fragments. The average size of the fragments can be, for example, less than about 5 cm, 4 cm, 3 cm, 2 cm, 1 cm, 9 mm, 8 mm, 7 mm, 6 mm, 5 mm, 4 mm, 3 mm, 2, mm, 1 mm, 0.5 mm, 0.1 mm or smaller, where the measurement reflects the largest dimension of length of the fragment. For example, the fragments can be about 0.5-2 mm or 1-2 mm. The maceration step can be performed using any means known in the art for such purpose, e.g., a maceration tank. In some embodiments, the maceration tank contains one or more grinder/maceration pumps at the bottom, and can be airtight and oxygen-free using nitrogen to replace the oxygen. As a non-limiting example, the tank can hold the solvent, including an aqueous solvent such as purified water, at a ratio of approximately 1 gallon to 1 pound (liquid extract to de-beaned coffee cherry). In some embodiments, "grinder pumps" can be used to pump the liquefied material to a sealed extraction vessel for extraction. For example, the maceration step can be carried out in a maceration tank under oxygen-free conditions.

In other embodiments, the de-beaned coffee cherries to be extracted can optionally be agitated (e.g., mixed). Agitation can be carried out by any method known in the art, for example by mechanical agitation (e.g., motor and blades), ultrasonic agitation (using, e.g., an ultrasonic transducer), and/or enzymatic agitation (e.g., by using introduced enzymes in accordance with methods known in the art). For example, the de-beaned coffee cherries can be agitated using mechanical agitation. Such mechanical agitation can be accomplished using a Lightnin agitator (Lightnin; Rochester, N.Y.). The de-beaned coffee cherries or fragments thereof if macerated can be agitated for a period of time, so as to facilitate the extraction process. For example, the mixture can be agitated for at least about 1 minute, 5 minutes, 10 minutes, 15 minutes, 20 minutes, 25 minutes, 30 minutes, 35 minutes, 40 minutes, 45 minutes, 50 minutes, 55 minutes, 1 hour, 1 hour 30 minutes, 2 hours, 3 hours or longer. The mixture can, for example, be agitated for about 30-40 minutes or longer.

The resulting extract can be filtered to remove particulate matter, including coffee cherry pulp sediment and/or skin pieces. Filtration methods are known in the art, and a person of ordinary skill can choose the appropriate filtration method from among those known. Non-limiting examples of such filtration methods include: 1) membrane filtration, such as microfiltration, ultrafiltration, nanofiltration, and reverse osmosis with either spiral-wound, stainless steel, ceramic, tubular, or plate-and-frame configurations; 2) sediment clarifying, whereby a food-grade tank can be employed to hold the extract under oxygen-free conditions to allow sediment to collect at the bottom of the tank due to gravity, e.g., for a period of about 1-24 or more hours, and removing the bottom sediment using, e.g., a separator valve; 3) press and filter methods, whereby a mechanical, pneumatic, or hydraulic press can be employed to squeeze the extract through a sieve or a series of sieves, or screen with less than 5 microns in size to eliminate sediment; 4) centrifugation, whereby a centrifuge can be used to separate the solids by centrifugal force; and 5) vacuum filtration, which can provide another oxygen-free filtration method. For example, the extract can be filtered using a press and filter method through a fine screen to remove any pulp or skin pieces. The filtrate can then be collected in a container such as a food-grade holding tank, in which it can be stored under oxygen-free conditions. The holding tank can also be used for clarifying/filtering by gravity separation (described below), or for overflow management, e.g., if too much liquid is being processed for the evaporators to keep up, or if the evaporators are operating at full capacity. Particulate matter can also or additionally be removed by sedimentation, i.e., by allowing the mixture to stand and the particulate matter to settle to the bottom of the storage vessel, using methods such as those described above. After sedimentation, the supernatant liquid is removed for further processing. The supernatant liquid can optionally be filtered. Sedimentation, if used, can also be conducted under oxygen-free conditions, for example under a blanket of inert gas. The fluids and filtrate at this point can be referred to as a dilute extract.

The particulate matter collected during filtration can optionally be processed further in a fruit/herb press, for example, a pneumatic press of 10 tons capacity (Eden Labs; Tacoma, Wash.), a hydraulic press, or similar device to generate additional fluid. The fluid generated by pressing the particular matter can then be added to the filtrate generated during the filtration step and added to the dilute extract.

Evaporating and Concentrating Coffee Fruit Extract

The dilute extract can be subjected to one or more evaporation steps. The evaporation step removes aqueous liquid content, and results in a more concentrated extract. Extract concentration is monitored using Brix measurements. Brix values are generally used to measure sugar concentration in a liquid, but they can also be used as a proxy for extract concentration, i.e., the higher the Brix value, the more concentrated the extract. The dilute extract can have a low Brix value, for example, less than about 10 Brix, 8 Brix, 6 Brix, 4 Brix, or lower, or between about 0.1 and 10 Brix, about 1 and about 5 Brix, about 1 and about 3 Brix, or about 3.5 and about 5 Brix, or from about 1.5 to about 2.5 Brix. The Brix value of the concentrated extract can be up to or at least about 1.5 Brix, 2.5 Brix, 5 Brix, 10 Brix, 15 Brix, 20 Brix X, 25 Brix, 30 Brix, 35 Brix, 40 Brix, 45 Brix, 50 Brix, 55 Brix, 60 Brix, 65 Brix, 70 Brix, 75 Brix, 80 Brix, 85 Brix, 90 Brix, 95 Brix, 100 Brix, or higher, or between about 30 and about 70 Brix, about 30 and about 60 Brix, about 30 and about 50 Brix, about 40 and about 60 Brix, or about 40 Brix or 50 Brix. The extract can be reduced by a ratio of up to about 5:1, about 10:1, about 15:1, about 20:1, about 25:1, about 35:1, about 40:1, about 45:1, about 50:1, about 60:1, or higher (where the ratio indicates initial versus final volume). Brix measurements can be conducted using a "Brix Meter" or "Refractometer." The liquid extract can be concentrated to any desired level, from a relatively dilute extract to a very concentrated and viscous extract and even subjected to complete evaporation (e.g., less than about 10% moisture content, or about 4-6% moisture content or below) to provide a dry extract concentrate.

The evaporation step can be conducted using any means and methods known in the art, for example, using a tube falling film evaporator, plate evaporator, a spinning band column evaporator, or a spinning cone evaporator. In a tube falling film evaporator, the liquid to be evaporated is distributed onto an upper tube sheet and onto heating tubes by an especially developed distribution system. From this system, the product flows downwards in the heating tubes to a lower tube sheet as a thin film. The evaporated vapor (steam) flows downwards in the same direction and consequently accelerates the flowing of the film. This limits the period of residence, during which the liquid to be evaporated is retained in the heating tube, to a few seconds. In a plate evaporator, the main feature is the compact design. The constructional height ranges from 3 to 5 meters depending on the design. Plate evaporators normally are designed for rising flow in single-pass operation. This keeps the thermal strain on the product as low as possible. Concentration of clear juice, or juice containing little pulp, are examples of application in the fruit juice industry. The spinning cone evaporator is a compact unit well-suited for the concentration of heat-sensitive, valuable and viscous products. It offers a short residence time, less thermal impact and greater processing flexibility than traditional rising or falling film evaporators. For example, the evaporation can be done using a spinning cone evaporator, such as Centritherm® evaporator (FT Technologies; Griffith, Australia). In exemplary embodiments, the evaporation step is conducted under low temperature conditions and/or at reduced pressure. As used herein, low temperature means a temperature less than or about 100° F., 90° F., 80° F., 70° F., 60° F., 50° F., or lower, or from about 50-100° F., 70-100° F., 50-80° F., 50-60° F., 60-70° F., 70-80° F., 80-90° F., or 90-100° F. For example, the evaporation can be done at a temperature of less than about 100° F. In some embodiments, the evaporation is performed under low temperature and oxygen-free conditions. In particular embodiments, evaporation can be carried out using vacuum-based techniques, e.g., using a vacuum concentrator to concentrate the liquid extract under low temperature conditions. The resulting concentrated extract can be stored under oxygen-free and/or refrigerated conditions, and can also be pasteurized if desired.

Evaporation can be performed in multiple steps, where after a certain amount of time has passed or a particular Brix concentration measurement has been reached, additional filtration steps described herein can be performed. For example, evaporation can be halted when the liquid extract reaches a Brix concentration of about 20 and filtered using a gravity sediment removal step, whereby a food-grade tank can be employed to hold the extract under oxygen-free conditions to allow sediment to collect at the bottom of the tank due to gravity, e.g., for a period of at least about 12 or more hours, and removing the bottom sediment. Evaporation can then be continued to further concentrate the liquid extract until a Brix concentration of about 40 is reached and filtered again using another gravity sediment removal step. Additional filtration steps ensure minimal particulate matter and high quality of concentrated fruit extract.

Once concentrated to the desired Brix level, the resulting extract is stored in a cool and dry place with no refrigeration required. The shelf-life of the liquid extract is about 18 months when stored at ambient room temperature conditions.

The liquid extract concentrate has a high amount of antioxidants such as polyphenols and other beneficial compounds and typically contains at least about 5% (w/w) total phenolic acids. For example, the liquid extract can comprise a total phenolic acid concentration of from about 5% to about 50% (w/w), about 10% to about 50% (w/w), about 15% to about 50% (w/w), about 20% to about 50% (w/w), about 5% to about 40% (w/w), about 10% to about 40% (w/w), about 15% to about 40% (w/w), about 20% to about 40% (w/w), about 5% to about 30% (w/w), about 10% to about 30% (w/w), about 15% to about 30% (w/w), about 20% to about 30% (w/w), about 5% to about 25% (w/w), about 10% to about 25% (w/w), about 15% to about 25% (w/w), about 20% to about 25% (w/w), about 5% to about 20% (w/w), about 10% to about 20% (w/w), about 15% to about 20% (w/w), about 5% to about 15% (w/w), about 10% to about 15% (w/w), about 5% to about 10% (w/w), or about or at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, or 95% (w/w).

Non-limiting examples of antioxidants include phenolic acids such as chlorogenic acid (CGA), caffeic acid, ferulic acid, isoferulic acid, dihydroferluic acid, quinic acid, hydroxycinnamic acids of various types, and combinations thereof. The term "chlorogenic acid" includes a family of esters of hydroxycinnamic acids (e.g., caffeic acid, ferulic acid, and p-coumaric acid) with quinic acid and isomers thereof such as caffeoylquinic acids (CQA), with 3 isomers (3-, 4-, and 5-CQA), dicaffeoylquinic acids (diCQA), with 3 isomers (3,4-diCQA; 3,5-diCQA; 4,5-diCQA), feruloylquinic acids (FQA), with 3 isomers (3-, 4- and 5-FQA); p-coumaroylquinic acids (pCoQA), with 3 isomers (3-, 4-, and 5-pCoQA), six mixed diesters of caffeoyl-feruloylquinic acids (CFAQ), diferuloylquinic acids, dimethoxycinamoylquinic acids, caffeoyl-dimethoxycinamoylquinic acids, feruloyl-dimethoxycinamoylquinic acids, and combinations thereof. Other beneficial compounds include, but are not limited to, phytochemicals (e.g., flavonoids), vitamins, and/or other nutrients such as prodelphinidins, procyanidins, trigonelline, lignins, tannins such as condensed tannins, coffee saccharides, anthocyanins, proanthocyanidins, and combinations thereof.

V. Process for Preparing Dried Coffee Fruit

In another aspect, the present invention provides a process for preparing dried coffee fruit that is rich in antioxidants and other beneficial compounds from de-beaned coffee cherries. In this process, coffee cherries are selected, de-beaned, optionally sprayed with a preservative coating, and dried with a dehydrator as described herein. The de-beaned coffee cherries can immediately begin the dehydration process or can be stored for later processing by refrigeration (e.g., freezing at a temperature of less than about −30° F. in a container such as a deoxygenated food-safe poly bag). In some embodiments, the de-beaned coffee cherries are sprayed with a preservative coating, but are not refrigerated (e.g., frozen at about −30° F.) before dehydrating. In other embodiments, the de-beaned coffee cherries are sprayed with a preservative coating and refrigerated (e.g., frozen at about −30° F.) before dehydrating. In yet other embodiments, the de-beaned coffee cherries are not sprayed with a preservative coating, but are refrigerated (e.g., frozen at about −30° F.). In still other embodiments, the de-beaned coffee cherries proceed to dehydration without a preservative coating spray or refrigeration (e.g., freezing at about −30° F.).

Drying Coffee Fruit

Drying of the coffee fruits, with or without protective spray/refrigeration steps, is achieved using one or more dehydration machines in a single step or multiple steps. In certain embodiments, the de-beaned coffee cherries are dehydrated to a lower water content, for example, to less than about 50%, 40%, 30%, 20%, 10%, 9%, 8%, 7%, 6%, 5%, 4%, 3%, 2%, or lower, by weight, in water content. For example, the coffee cherries can have a water content of about 4% (w/w) or less after dehydration (e.g., about 2% by weight for tea products). Any method known in the art for dehydrating food samples, including any suitable conditions of time and temperature, can be used with the processes disclosed herein. For example, the dehydration can be done under low heat, for example, up to or about 100° F., 105° F., 110° F., 115° F., 120° F., 125° F., 130° F., 135° F., 140° F., 145° F., 150° F., 160° F., 180° F., or 200° F., or higher, or between about 100-200° F., about 100-150° F., about 120-170° F., about 130-160° F., or about 130-150° F. In particular embodiments, the dehydration is performed under low heat at a temperature of less than about 125° F. The dehydration can be done for a period of time, for example, at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 24 hours, 48 hours, or longer. For example, dehydration can be done at a temperature of less than about 125° F. for about 10-12 hours, or until the desired water content is achieved. In some embodiments, the dehydration step can be carried out under oxygen-free conditions, for example, by exposing the de-beaned coffee cherries to an inert gas such as nitrogen during dehydration.

In exemplary embodiments, the dehydration is carried out in two dehydration steps. For example, the first dehydration step (e.g., using a refrigerated air/condenser/dryer system under low heat or a stainless steel mesh belt dryer) reduces the water content of the de-beaned coffee cherries from about 85%-90% to about 10%, and the second dehydration step (e.g., using a finish dryer) further reduces the water content from about 10% to about 4% or less. The second dehydrator can optionally pasteurize the dehydrated coffee cherries using microwaves (approximately 1-2 or more hours using the methods disclosed herein). Alternatively, a centrifuge can be used to reduce the water content of the de-beaned coffee cherries.

The de-beaned coffee cherries can be conveyed to the (first) dehydrator using a shaker/vibrator conveyor, or loaded directly into the dehydrator. Once dehydrated, the dried coffee fruit product is stored in a cool and dry place with no refrigeration required. The shelf-life of the dried coffee fruit is about 18 months when stored at ambient room temperature conditions.

In certain embodiments, the de-beaned coffee cherries, with or without protective spray/refrigeration steps, are shredded to a size of from about 3 mm to about 10 mm using a shredding machine such as a "Toro Brand" leaf shredder or a mechanically similar machine such as a stainless steel "WATERFALL" shredder (COMMERCIAL brand model NS-26). The shredded coffee fruit can travel by air, gravity, and/or conveyors into a heated air cyclone to quickly pre-dry the coffee fruit to a moisture level of about 10% to about 15% from an initial moisture level of about 85% to about 90%. The coffee fruit can then travel to a second dehydrator (e.g., a finish dryer) that uses gas, solar, electricity, and/or microwaves for finish drying and pasteurizing. In some embodiments, the optional shredding step can be enhanced by reducing the surrounding oxygen by tenting the air intakes to the shredder and cyclone and replacing oxygen with nitrogen via a nitrogen generator.

After dehydration of the de-beaned coffee cherries (e.g., after either the first or second dehydration step if two dehydration steps are used), the dried coffee fruit can be subjected to an optional enrichment step to fortify the dried fruit product with antioxidants and other beneficial compounds. This enrichment step can involve contacting the dehydrated coffee cherries with an enriching substance, such as a liquid coffee fruit extract prepared using the process disclosed herein. Such contacting can be carried out by, for example, spraying the dehydrated cherries with an aqueous or other extract. For example, when the de-beaned coffee cherries that are dehydrating have reached a moisture content of about 4%, the dehydrated coffee cherries can be sprayed with a liquid coffee fruit extract prepared as described herein or using methods known in the art, to enrich the dehydrated de-beaned coffee cherry product. In certain instances, the spray amount can be about 0.1, 0.5, 0.75, 1, 1.25, 1.5, 2, 3, 4, 5, 6, 7, 8, 9, 10, 15, 20, 25, 30, 35, 40, 45, 50, or more ounces of extract per kilogram of dehydrated coffee fruit. For example, the spray amount can be about 1 ounce of 40 Brix liquid coffee fruit extract for every kilogram of dried coffee fruit (based on about 4% moisture level).

In certain embodiments, the dried coffee fruit is further processed to a powdered form after dehydration using any grinding or powder-creating machine known in the art such as a Fitzmill (e.g., Fitzmill DAS-06 available from IDEX MPT Inc.). In some instances, mesh screens of varying sizes (e.g., screen sizes #20, 30, 40, 50, 60, 70, 80, 90, 100, etc.) are used to grind the dried coffee fruit into a powder and obtain particles of the desired size and uniformity. For example, the #40 screen size creates a powder with a medium particle size. In other instances, micro-grinding machines are used to finely grind the dried coffee fruit to the size of flour particles. The particles present in the coffee fruit powder typically have a median or mean particle size ranging from about 100 µm to about 500 µm, e.g., about 250 µm to about 500 µm, about 200 µm to about 425 µm, about 300 µm to about 500 µm, about 100 µm to about 300 µm, or about 100 µm, 150 µm, 200 µm, 250 µm, 300 µm, 350 µm, 400 µm, 450 µm, or 500 µm.

In particular embodiments, the coffee fruit powder prepared from dried coffee fruit as described herein comprises a total phenolic acid concentration of from about 5% to about 25% (w/w), e.g., about 5% to about 20% (w/w), about 5% to about 15% (w/w), about 7% to about 15% (w/w), about 7% to about 12% (w/w), about 10% to about 25% (w/w), about 10% to about 20% (w/w), about 10% to about 15% (w/w), about 15% to about 25% (w/w), about 20% to about 25% (w/w), or about or at least about 5%, 6%, 7%, 8%, 9%, 10%, 11%, 12%, 13%, 14%, 15%, 16%, 17%, 18%, 19%, 20%, 21%, 22%, 23%, 24%, or 25% (w/w). In certain instances, the phenolic acids present in the coffee fruit powder include, but are not limited to, chlorogenic acid, caffeic acid, ferulic acid, isoferulic acid, dihydroferulic acid, quinic acid, and combinations thereof.

VI. Process for Preparing Powder from Coffee Fruit Extract

In yet another aspect, the present invention provides a process for drying a liquid coffee fruit extract to produce a concentrated powder suitable for human consumption and other uses. In this process, coffee cherries are selected, de-beaned, and the antioxidants and other nutrients of the fruit are extracted according to the method described herein to product a liquid extract. The liquid extract can be concentrated to a Brix value of about 40, and then subjected to a drying process to prepare a concentrated powder. In some embodiments, the drying process is a spray dry process. In particular embodiments, the drying process is a pulse dry process. Other drying processes include, but are not limited to, vacuum microwave, freeze-drying, and air-drying methods.

Pulse drying is a process that uses flash atomization to prepare dried powders with a speeding jet of hot gas. For example, the pulse drying process can comprise a rhythmic, pulsing action by a super-heated gas to produce particles with desired properties such as particle size, particle size distribution, and particle shape. When compared to spray dryers, pulse dryers dry the liquid of interest in a fraction of the time with significantly improved thermal efficiencies and with particle characteristics that cannot be achieved with spray dryers. Pulse drying systems generally include a drying chamber, cyclone, and bag housing, and are available from, e.g., Wave Dry (Corte Madera, Calif.).

The process of drying the liquid extract described herein into a powder protects heat-sensitive nutrients present in the extract. The resulting powder is particularly advantageous over powders prepared from conventionally dried fruit because it is prepared using a concentrated liquid extract (e.g., about 40 Brix value) containing a higher level of beneficial compounds including antioxidants and polyphenols that are of interest in nutrition and human health. The finished product is stored in a cool and dry place, and requires no refrigeration.

The powder form of the liquid extract typically contains at least about 5% (w/w) total phenolic acids. For example, the powder prepared by the process described herein can comprise a total phenolic acid concentration of from about 5% to about 50% (w/w), about 10% to about 50% (w/w), about 15% to about 50% (w/w), about 20% to about 50% (w/w), about 5% to about 40% (w/w), about 10% to about 40% (w/w), about 15% to about 40% (w/w), about 20% to about 40% (w/w), about 5% to about 30% (w/w), about 10% to about 30% (w/w), about 15% to about 30% (w/w), about 20% to about 30% (w/w), about 5% to about 25% (w/w), about 10% to about 25% (w/w), about 15% to about 25% (w/w), about 20% to about 25% (w/w), about 5% to about 20% (w/w), about 10% to about 20% (w/w), about 15% to about 20% (w/w), about 5% to about 15% (w/w), about 10% to about 15% (w/w), about 5% to about 10% (w/w), or about or at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, or 95% (w/w).

VII. Coffee Fruit Products and Compositions

In certain aspects, the present invention provides coffee fruit products including liquid extracts, dried fruit, and powders prepared by the methods described herein. In certain other aspects, the present invention provides compositions including beverages, foods, neutraceuticals, and cosmetics comprising one or more of the coffee fruit products prepared by the methods described herein. The coffee fruit products and compositions containing them advantageously contain high levels of powerful antioxidants capable of reducing oxidation and preventing oxidative damage for the prevention or treatment of a vast array of diseases and conditions including, but not limited to, cancer, Alzheimer's disease, atherosclerosis, skin aging, ocular disease, and drug-induced toxicity.

In some embodiments, the coffee fruit product is a liquid coffee fruit extract. In particular embodiments, the liquid extract comprises a total phenolic acid concentration of at least about 5% (w/w). For example, the liquid extract can comprise a total phenolic acid concentration of from about 5% to about 50% (w/w), about 10% to about 50% (w/w), about 15% to about 50% (w/w), about 20% to about 50% (w/w), about 5% to about 40% (w/w), about 10% to about 40% (w/w), about 15% to about 40% (w/w), about 20% to about 40% (w/w), about 5% to about 30% (w/w), about 10% to about 30% (w/w), about 15% to about 30% (w/w), about 20% to about 30% (w/w), about 5% to about 25% (w/w), about 10% to about 25% (w/w), about 15% to about 25% (w/w), about 20% to about 25% (w/w), about 5% to about 20% (w/w), about 10% to about 20% (w/w), about 15% to about 20% (w/w), about 5% to about 15% (w/w), about 10% to about 15% (w/w), about 5% to about 10% (w/w), or about or at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, or 95% (w/w). In certain instances, the coffee fruit extract has a Brix value of about 40. In other instances, the phenolic acids present in the coffee fruit extract include, but are not limited to, chlorogenic acid, caffeic acid, ferulic acid, isoferulic acid, dihydroferulic acid, quinic acid, and combinations thereof.

In other embodiments, the coffee fruit product is dried coffee fruit. In certain instances, the dried coffee fruit is a loose-leaf antioxidant tea that can be reconstituted in, e.g., hot water, for consumption as a beverage containing high levels of antioxidants including the phenolic acids described herein.

In yet other embodiments, the coffee fruit product is a coffee fruit powder. The coffee fruit powder can comprise a total phenolic acid concentration of from about 5% to about 25% (w/w), e.g., about 5% to about 20% (w/w), about 5% to about 15% (w/w), about 7% to about 15% (w/w), about 7% to about 12% (w/w), about 10% to about 25% (w/w), about 10% to about 20% (w/w), about 10% to about 15% (w/w), about 15% to about 25% (w/w), about 20% to about 25% (w/w), or about or at least about 5%, 6%, 7%, 8%, 9%, 10%, 11%, 12%, 13%, 14%, 15%, 16%, 17%, 18%, 19%, 20%, 21%, 22%, 23%, 24%, or 25% (w/w). In certain instances, the phenolic acids present in the coffee fruit powder include, but are not limited to, chlorogenic acid, caffeic acid, ferulic acid, isoferulic acid, dihydroferulic acid, quinic acid, and combinations thereof.

In certain instances, the coffee fruit powder is a super-concentrated dry product containing high levels of antioxidants prepared from the liquid coffee fruit extract described herein. In other instances, the coffee fruit powder is a fortified or enriched coffee fruit powder prepared by contacting (e.g., spraying) dried coffee fruit with the liquid coffee fruit extract prior to grinding dried coffee fruit into a powder.

The compositions comprising one or more of the coffee fruit products described herein can be ingested or topically applied by a human and/or animal for nutritional, feed supplement, health-maintenance, health-improvement, and/or recreational purpose. Non-limiting examples of compositions for consumption include solid products (e.g., dietary supplements, snack bars, neutraceuticals, etc.) and liquid products (e.g., juices, sports drinks, carbonated beverages, teas, and other beverages, syrups, elixirs, etc.). Non-limiting examples of compositions for topical use include skin care products, anti-aging products, and other cosmetics.

VIII. EXAMPLES

The following examples are provided in order to better enable one of ordinary skill in the art to make and use the disclosed compositions and methods, and are not intended to limit the scope of the invention in any way.

Example 1

Preparation of Coffee Fruit Extract

After removal of the coffee bean, the remaining coffee fruit (skin, pulp, and mucilage) retains many nourishing compounds including antioxidants, polyphenols, phytochemicals, vitamins, etc. that are of interest in nutrition and human health. The following example provides a process for extracting and concentrating the nutrients of the coffee fruit to produce a liquid extract suitable for human consumption and other uses.

Selection of Desirable Coffee Cherries

The process begins with whole coffee cherries that are washed and "floated." Undesirable cherries, such as overripe and underdeveloped coffee cherries float, whereas ripe and desirable coffee cherries do not. Thus, "floating" plus visual inspection allow for the easy removal of undesirable cherries.

Pulping Coffee Cherry and Preparing Fruit for Extraction

After selection of ripe coffee cherries, the cherries are then de-seeded (pulped). The remaining coffee fruits (skin, pulp, and mucilage) are transported a short distance (within 100 yards of the pulping area) via a PVC pipe (or similar rapid food-safe transport) using clean filtered water as a transport medium.

Optionally, after de-seeding the pulped cherries (coffee fruits) can be sprayed with a mist comprising or consisting of a mixture of ascorbic acid and citric acid in water. For example, the aqueous solution of ascorbic acid and citric acid can be prepared by mixing ½ cup ascorbic acid and ¼ cup citric acid per gallon of water. Generally, the mist is applied to the coffee fruits as they leave the pulping machine. Without being bound by any particular theory, the inclusion of this step slows the oxidation (browning) of the coffee fruits, thereby extending the working time of the coffee fruits before the fruits degrade.

Once the cherries are pulped and transferred, a press/extruder is used to remove the excess water on the coffee fruits that was introduced during the transport from the pulper area to the press/extruder area. Optionally, excess water is removed by using a vibration screen or centrifuge. All excess water can be collected and pumped back to the pulping area for reuse.

Next, the coffee fruits are immediately bagged into food-safe poly bags and sealed. Oxygen is removed from the bags using a vacuum pump since any remaining oxygen in the bags can react with the coffee fruits to degrade the desirable antioxidants. The sealed vacuumed bags are immediately placed at −30° Fahrenheit (F) for about 24 hours to irreversibly denature enzymes that degrade the coffee fruits.

Extracting Coffee Fruit Nutrients

Frozen coffee fruits are slowly brought from −30° F. to +30° F. in a controlled temperature room overnight. Coffee fruits at +30° F. are further thawed by adding them to 180° F. filtered hot water. Once added to the hot water, the coffee fruits are mixed, agitated, or macerated (chopped or ground into small pieces) in the hot water. Optionally, the hot water is de-ionized.

Without being bound by any particular theory, the large change in temperature when the coffee fruits are added to the hot water causes the cells of the coffee fruit to "burst," releasing the nutrients from inside the cells. The step of mixing, agitating, or macerating the coffee fruits in the hot water aids in the extraction process, particularly the macerating step, which allows more contact of the coffee fruit surface with the water. Macerating can be achieved by a number of machines including a grinder-pump or a sheer-pump.

The coffee fruits are incubated and the nutrients are extracted in the hot water with mixing, agitation, or maceration for about 20-40 minutes.

After extraction of the nutrients, the resulting "Tea" and saturated fruit (skins and pulp) are transferred from the extraction tanks to a press/extruder to remove all remaining "Tea" from the saturated skins and pulp. The resulting "Tea" is next filtered through a fine screen to remove the pulp and skin pieces.

Evaporating and Concentrating Coffee Fruit Nutrients

The isolated "Tea" is collected in a food-safe liquid tote (IBC) and is held for a minimum of 1 hour. The 1 hour incubation allows any sediment/pulp to separate by gravity.

Any sediment that collects is removed. At this point the "Tea" contains a measurable refractive index between 3.5 and 5 Brix.

Concentration of the "Tea" is achieved at low temperatures (e.g., under 100° F.) using a vacuum concentrator which allows the "Tea" to boil at close to room temperature. The vacuum concentrator evaporates the "Tea" until the Brix Measurement reaches 20. After reaching a higher concentration, a second gravity sedimentation step is included to remove any additional pulp or skin. After about 12 hours any sediment that collects is removed and the vacuum concentration process continues until the measured concentration reaches 40 Brix, the desired finished value. Finally, a third gravity sedimentation step is performed, and sediment is removed. Optionally, the 40 Brix concentrated "Tea" can be pasteurized by transferring the "Tea" to a pasteurizing machine where the "Tea" is very quickly heated and cooled.

Once concentration, final gravity sedimentation, and optional pasteurization is complete, the "Tea" is placed into new sterile food-safe IBC totes and stored in cool and dry conditions. The finished product needs no refrigeration.

Product Specification for Liquid Extract

The following table provides the product specification for an exemplary liquid coffee fruit extract prepared according to the method described herein.

| PHYSICAL PROFILE | SPECIFICATION |
| --- | --- |
| Concentration | 40 Brix |
| PRODUCT PROFILE | SPECIFICATION |
| Solids | <2% Maximum |
| Solubility | >98% Soluble in Water |
| Total Phenolic Acids* | 20% Minimum |
| Caffeine | 0.7 to 1.1% p/.5 ml |
| MICROBIOLOGICAL PROFILE | SPECIFICATION |
| Total Bacterial Count | 0 cfu/g |
| Yeast and Mold | 0 cfu/g |
| Coliforms | Negative |
| E. Coli | Negative |
| INGREDIENT STATEMENT | SHELF LIFE |
| Coffee Fruit Extract | 18 Months |

*Chlorogenic Acid, Caffeic Acid, Ferulic Acid, Isoferulic Acid, Dihydroferulic Acid, Quinic Acid Example 2

Preparation of Dried Coffee Fruit

After removal of the coffee bean, the remaining coffee fruit (skin, pulp, and mucilage) retains many nourishing compounds including antioxidants and polyphenols that are of interest in nutrition and human health. The following example provides a process for drying the coffee fruit to produce dried skins and powders suitable for human consumption and other uses.

Selection of Desirable Coffee Cherries

The process begins with whole coffee cherries that are washed and "floated." Undesirable cherries, such as overripe and underdeveloped coffee cherries float, whereas ripe and desirable coffee cherries do not. Thus, "floating" plus visual inspection allow for the easy removal of undesirable cherries.

Pulping Coffee Cherry and Preparing Fruit for Drying

After selection of ripe coffee cherries, the cherries are then de-seeded (pulped). The remaining coffee fruits (skin, pulp, and mucilage) are transported a short distance (within 100 yards of the pulping area) via a PVC pipe (or similar rapid food-safe transport) using clean filtered water as a transport medium.

Optionally, after de-seeding the pulped cherries (coffee fruits) can be sprayed with a mist comprising or consisting of a mixture of ascorbic acid and citric acid in water. For example, the aqueous solution of ascorbic acid and citric acid can be prepared by mixing ½ cup ascorbic acid and ¼ cup citric acid per gallon of water. Generally, the mist is applied to the coffee fruits as they leave the pulping machine. Without being bound by any particular theory, the inclusion of this step slows the oxidation (browning) of the coffee fruits, thereby extending the working time of the coffee fruits before the fruits degrade.

Once the cherries are pulped and transferred, a press/extruder is used to remove the excess water on the coffee fruits that was introduced during the transport from the pulper area to the press/extruder area. Optionally, excess water is removed by using a vibration screen or centrifuge. All excess water can be collected and pumped back to the pulping area for reuse.

After removing excess water, the coffee fruits are immediately sent (e.g., via a stainless steel auger or a food safe conveyor) to a dehydration machine.

Optionally, before further processing, the coffee fruits can be preserved for later processing by immediately bagging into food-safe poly bags, sealing, vacuuming, and freezing at −30° F. Vacuuming removes the remaining oxygen in the sealed bags, which can react with the fruits to degrade the desirable antioxidants. Freezing the bags at −30° F. for about 24 hours may irreversibly denature enzymes that degrade the coffee fruit. Frozen coffee fruits can be slowly brought from −30° F. to +30° F. in a controlled temperature room overnight.

Drying Coffee Cherries

The coffee fruits can be dried in a dehydration machine that uses a refrigerated air/condenser/dryer system which allows for drying of the fruit using low heat (under 125° F.), retaining the nutrients of the coffee fruits. The dehydration machine is used to dry the coffee fruit from about 85% moisture level to about 10% moisture level. Once at about 10% moisture level, the coffee fruits are transferred to a finish dryer which pasteurizes the fruits using microwaves and dries them from about 10% moisture level to the desired moisture level, usually from about 2% to about 4%. Typically, this drying process can produce about 250 kg of finished product per day.

Alternatively, a stainless steel mesh belt dryer is used in place of a dehydration machine to dry the coffee fruit from about 85% moisture level to about 10% moisture level. Once at about 10% moisture level, the coffee fruits are transferred to a finish dryer which pasteurizes the fruits using microwaves and dries them from about 10% moisture level to the desired moisture level, usually from about 2% to about 4%. Typically, this drying process can produce over 1 ton of finished product per day.

After completing the drying process, the dried fruits are now transferred to a batch tank where they rest until they are used as dried skins or ground into a powder, depending on the preference of the consumer. The finished product is stored in a cool and dry place, and requires no refrigeration.

Product Specification for Dried Powder

The following table provides the product specification for an exemplary dried coffee fruit powder prepared according to the method described herein.

| PHYSICAL PROFILE | SPECIFICATION |
|---|---|
| Particle Analysis | 100% through a #40 screen |
| PRODUCT PROFILE | SPECIFICATION |
| Solids Solubility | 90% Minimum Partially Soluble in Water |
| Total Phenolic Acids* | 7-12% |
| Caffeine | 0.7 to 1.1% p/.5 ml |
| MICROBIOLOGICAL PROFILE | SPECIFICATION |
| Total Aerobic Count | 0 cfu/g |
| Yeast and Mold | 540 cfu/g |
| Coliforms | <10 cfu/g |
| E. Coli | Negative |
| INGREDIENT STATEMENT | SHELF LIFE |
| Dried Coffee Fruit Powder | 18 Months |

*Chlorogenic Acid, Caffeic Acid, Ferulic Acid, Isoferulic Acid, Dihydroferulic Acid, Quinic Acid Example 3

Preparation of Powder from Coffee Fruit Extract

The following example provides a process for drying a coffee fruit extract to produce a concentrated powder suitable for human consumption and other uses.

A liquid coffee fruit extract prepared according to Example 1 can be dried to a powder by a pulse dry process. This process spray dries the extract and protects heat-sensitive nutrients present in the extract. The resulting product is particularly advantageous over powders prepared from conventionally dried skins because it is prepared using a concentrated liquid extract (e.g., 40 Brix value) containing a higher concentration of compounds including antioxidants and polyphenols that are of interest in nutrition and human health. The finished product is stored in a cool and dry place, and requires no refrigeration.

Example 4

Properties of Coffee Fruit Powder

The following example illustrates some of the numerous advantageous properties exhibited by the dried coffee fruit powder prepared according to the method described herein.

Cell Viability Assay

The cell viability assay (CVA) is based on a proliferation assay that determines the effect of the powder of the present invention on cell growth and cell viability. The assay result is expressed as the maximum concentration of powder present in cell culture that promotes cell viability using adenosine triphosphate (ATP) as a marker for metabolically active cells.

| | Effective Concentration |
|---|---|
| CVA Result | 1321.25 µg/ml |

Cellular Anti-Inflammatory Assay

The cellular anti-inflammatory assay (NFκB) determines the inhibition potential of the powder of the present invention on expression/production level of NFκB in human cells. NFκB serves as a biomarker for inflammation.

In particular, this assay determines the anti-inflammatory potential of the powder in human cells. NFκB (Nuclear Factor kappa B), a protein complex that is involved in cellular responses to stimuli such as stress and free radicals, is used as inflammation biomarker.

In this assay, tumor necrosis factor alpha (TNF-α), a pleiotropic inflammatory cytokine, is introduced to the human cells to trigger cellular inflammation. If an anti-inflammatory material is presented in the cellular environment, the material inhibits NFκB activation and the degree of inhibition can be monitored via NFκB expression. The NFκB expression level of the human cells, treated with and without the powder of the present invention, under the stressed condition are therefore monitored and compared. Maximum percentage of NFκB expression inhibition induced by the powder is shown in the table below. The concentration used that induced the maximum inhibition of NFκB expression is also shown.

| | Inducer/Stressor | Maximum inhibition | Effective Concentration |
|---|---|---|---|
| NFκB Assay Result | TNF-α | 67.01% | 1321.25 µg/ml |

Cellular Antioxidant Assay

The cellular antioxidant assay (CAA) analyzes the capacity of the powder of the present invention to protect a fluorescent probe (as a marker) from damage by reactive oxygen species (ROS) in an intracellular environment. In this assay, a peroxyl radical is used as the ROS, and human liver cells are used as the cellular model. Quercetin is used as the standard, and the results are expressed as µmole quercetin equivalency (µmole QE) per gram (or milliliter) of the powder.

| | Effective Concentration |
|---|---|
| CAA Result | 431.82 µmole QE/gram |

IX. EXEMPLARY EMBODIMENTS

Exemplary embodiments provided in accordance with the presently disclosed subject matter include, but are not limited to, the claims and the following embodiments:

1. A method for preparing a coffee fruit extract, the method comprising:
   (a) providing de-beaned coffee cherries;
   (b) freezing the de-beaned coffee cherries under substantially oxygen-free conditions at a temperature of less than about −30° Fahrenheit (F) to produce frozen de-beaned coffee cherries;
   (c) thawing the frozen de-beaned coffee cherries to produce thawed de-beaned coffee cherries; and
   (d) extracting antioxidants from the thawed de-beaned coffee cherries in a heated aqueous solvent to produce a coffee fruit extract and extracted de-beaned coffee cherries.
2. The method of embodiment 1, wherein the de-beaned coffee cherries consist of skin, pulp, and mucilage.

3. The method of embodiment 1 or 2, wherein the antioxidants comprise one or more phenolic acids, proanthocyanidins, other phytochemicals and/or nutrients, or combinations thereof.
4. The method of embodiment 3, wherein the one or more phenolic acids are selected from the group consisting of chlorogenic acid, caffeic acid, ferulic acid, isoferulic acid, dihydroferulic acid, quinic acid, and combinations thereof.
5. The method any one of embodiments 1 to 4, further comprising promptly contacting the de-beaned coffee cherries with a coating comprising ascorbic acid and citric acid to produce coated de-beaned coffee cherries prior to freezing them.
6. The method of any one of embodiments 1 to 5, wherein the de-beaned coffee cherries are frozen at a temperature of about −30° F.
7. The method of any one of embodiments 1 to 6, wherein the frozen de-beaned coffee cherries are thawed at a temperature of about 30° F.
8. The method of any one of embodiments 1 to 7, wherein the antioxidants are extracted by mixing, agitating, or macerating the thawed de-beaned coffee cherries in the heated aqueous solvent.
9. The method of any one of embodiments 1 to 8, wherein the heated aqueous solvent comprises purified water.
10. The method of embodiment 9, wherein the purified water is heated to a temperature of about 180° F.
11. The method of any one of embodiments 1 to 10, further comprising pressing the extracted de-beaned coffee cherries with the coffee fruit extract to produce a pressed coffee fruit extract.
12. The method of embodiment 11, further comprising filtering the pressed coffee fruit extract to produce a filtered coffee fruit extract.
13. The method of embodiment 12, wherein the filtered coffee fruit extract has a Brix value of between about 3.5 to about 15.
14. The method of embodiment 12 or 13, further comprising separating and removing any sediment or pulp from the filtered coffee fruit extract.
15. The method of any one of embodiments 12 to 14, further comprising concentrating the filtered coffee fruit extract to produce a concentrated coffee fruit extract.
16. The method of embodiment 15, wherein the filtered coffee fruit extract is concentrated using a vacuum evaporator at a temperature of less than about 100° F.
17. The method of embodiment 15 or 16, further comprising separating and removing any sediment when the concentrated coffee fruit extract reaches a Brix value of about 20.
18. The method of embodiment 17, wherein the concentrated coffee fruit extract is further concentrated to a Brix value of about 40 to produce the coffee fruit extract.
19. The method of embodiment 18, wherein the coffee fruit extract has a total phenolic acid concentration of at least about 5% (w/w) or at least about 20% (w/w).
20. The method of embodiment 19, wherein the total phenolic acid concentration comprises a mixture of chlorogenic acid, caffeic acid, ferulic acid, isoferulic acid, dihydroferulic acid, and quinic acid.
21. A method for preparing a dried coffee fruit product, the method comprising:
(a) providing de-beaned coffee cherries;
(b) dehydrating the de-beaned coffee cherries to produce partially dried de-beaned coffee cherries having a moisture level of from about 10% to about 15%; and
(c) dehydrating the partially dried de-beaned coffee cherries to produce a dried coffee fruit product having a moisture level of from about 2% to about 4%.
22. The method of embodiment 21, wherein the de-beaned coffee cherries consist of skin, pulp, and mucilage.
23. The method of embodiment 21 or 22, wherein the dried coffee fruit product comprises antioxidants.
24. The method of embodiment 23, wherein the antioxidants comprise one or more phenolic acids, proanthocyanidins, other phytochemicals and/or nutrients, or combinations thereof.
25. The method of embodiment 24, wherein the one or more phenolic acids are selected from the group consisting of chlorogenic acid, caffeic acid, ferulic acid, isoferulic acid, dihydroferulic acid, quinic acid, and combinations thereof.
26. The method of any one of embodiments 21 to 25, further comprising promptly contacting the de-beaned coffee cherries with a coating comprising ascorbic acid and citric acid to produce coated de-beaned coffee cherries prior to dehydrating them.
27. The method of any one of embodiments 21 to 26, further comprising freezing the de-beaned coffee cherries under substantially oxygen-free conditions at a temperature of less than about −30° Fahrenheit (F) to produce frozen de-beaned coffee cherries prior to dehydrating them.
28. The method of embodiment 27, wherein the de-beaned coffee cherries are frozen at a temperature of about −30° F.
29. The method of embodiment 27 or 28, further comprising thawing the frozen de-beaned coffee cherries to produce thawed de-beaned coffee cherries prior to dehydrating them.
30. The method of embodiment 29, wherein the frozen de-beaned coffee cherries are thawed at a temperature of about 30° F.
31. The method of any one of embodiments 21 to 30, wherein the de-beaned coffee cherries are shredded prior to dehydrating them.
32. The method of any one of embodiments 21 to 31, wherein the de-beaned coffee cherries have a moisture level of from about 85% to about 90% prior to dehydrating them.
33. The method of any one of embodiments 21 to 32, wherein the de-beaned coffee cherries are partially dried using a cold dehydrator at a temperature of less than about 125° F.
34. The method of any one of embodiments 21 to 32, wherein the de-beaned coffee cherries are partially dried using a stainless steel mesh belt dryer or a heated air cyclone.
35. The method of any one of embodiments 21 to 34, wherein the partially dried de-beaned coffee cherries are dried using a finish dryer.
36. The method of any one of embodiments 21 to 35, further comprising contacting the dried coffee fruit product with a coffee fruit extract to fortify the dried coffee fruit product.

37. The method of embodiment 36, wherein the coffee fruit extract is prepared by the method of any one of embodiments 1 to 20.

38. The method of any one of embodiments 21 to 37, further comprising grinding the dried coffee fruit product to produce a coffee fruit powder.

39. The method of embodiment 38, wherein the coffee fruit powder has a total phenolic acid concentration of from about 7% to about 12% (w/w).

40. The method of embodiment 39, wherein the total phenolic acid concentration comprises a mixture of chlorogenic acid, caffeic acid, ferulic acid, isoferulic acid, dihydroferulic acid, and quinic acid.

41. The method of any one of embodiments 38 to 40, wherein the coffee fruit powder promotes cell growth and cell viability.

42. The method of any one of embodiments 38 to 41, wherein the coffee fruit powder inhibits NFκB expression in human cells.

43. A method for preparing a coffee fruit powder, the method comprising drying a coffee fruit extract prepared by the method of any one of embodiments 1 to 20.

44. The method of embodiment 43, wherein drying the coffee fruit extract is performed using a pulse drying system.

45. A coffee fruit extract prepared by the method of any one of embodiments 1 to 20.

46. A dried coffee fruit product prepared by the method of any one of embodiments 21 to 37.

47. A coffee fruit powder prepared by the method of any one of embodiments 38 to 44.

48. A composition comprising the coffee fruit extract of embodiment 45.

49. A composition comprising the dried coffee fruit product of embodiment 46.

50. A composition comprising the coffee fruit powder of embodiment 47.

51. The composition of any one of embodiments 48 to 50, wherein the composition is a dietary supplement, snack bar, neutraceutical, juice, sports drink, carbonated beverage, or tea.

52. The composition of any one of embodiments 48 to 50, wherein the composition is a skin care product, anti-aging product, or other cosmetic product.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described. All publications, patents, and patent applications cited in this specification are herein incorporated by reference as if each individual publication, patent, or patent application were specifically and individually indicated to be incorporated by reference.

What is claimed is:

1. A method for preparing a coffee fruit extract having antioxidant activity, the method comprising:
   (a) providing de-beaned coffee cherries;
   (b) freezing the de-beaned coffee cherries under substantially oxygen-free conditions at a temperature of less than about −30° Fahrenheit (F) to produce frozen de-beaned coffee cherries;
   (c) thawing the frozen de-beaned coffee cherries to produce thawed de-beaned coffee cherries; and
   (d) extracting antioxidants from the thawed de-beaned coffee cherries in a heated aqueous solvent to produce a coffee fruit extract having antioxidant activity and extracted de-beaned coffee cherries.

2. The method of claim 1, wherein the de-beaned coffee cherries consist of skin, pulp, and mucilage.

3. The method of claim 1, wherein the antioxidants comprise one or more phenolic acids, proanthocyanidins, other phytochemicals and/or nutrients, or combinations thereof.

4. The method of claim 3, wherein the one or more phenolic acids are selected from the group consisting of chlorogenic acid, caffeic acid, ferulic acid, isoferulic acid, dihydroferulic acid, quinic acid, and combinations thereof.

5. The method claim 1, further comprising promptly contacting the de-beaned coffee cherries with a coating comprising ascorbic acid and citric acid to produce coated de-beaned coffee cherries prior to freezing them.

6. The method of claim 1, wherein the de-beaned coffee cherries are frozen at a temperature of about −30° F.

7. The method of claim 1, wherein the frozen de-beaned coffee cherries are thawed at a temperature of about 30° F.

8. The method of claim 1, wherein the antioxidants are extracted by mixing, agitating, or macerating the thawed de-beaned coffee cherries in the heated aqueous solvent.

9. The method of claim 1, wherein the heated aqueous solvent comprises purified water.

10. The method of claim 9, wherein the purified water is heated to a temperature of about 180° F.

11. The method of claim 1, further comprising pressing the extracted de-beaned coffee cherries with the coffee fruit extract to produce a pressed coffee fruit extract.

12. The method of claim 11, further comprising filtering the pressed coffee fruit extract to produce a filtered coffee fruit extract.

13. The method of claim 12, wherein the filtered coffee fruit extract has a Brix value of between about 3.5 to about 15.

14. The method of claim 12, further comprising separating and removing any sediment or pulp from the filtered coffee fruit extract.

15. The method of claim 12, further comprising concentrating the filtered coffee fruit extract to produce a concentrated coffee fruit extract.

16. The method of claim 15, wherein the filtered coffee fruit extract is concentrated using a vacuum evaporator at a temperature of less than about 100° F.

17. The method of claim 15, further comprising separating and removing any sediment when the concentrated coffee fruit extract reaches a Brix value of about 20.

18. The method of claim 17, wherein the concentrated coffee fruit extract is further concentrated to a Brix value of about 40 to produce the coffee fruit extract.

19. The method of claim 18, wherein the coffee fruit extract has a total phenolic acid concentration of at least about 5% (w/w).

20. The method of claim 19, wherein the total phenolic acid concentration comprises a mixture of chlorogenic acid, caffeic acid, ferulic acid, isoferulic acid, dihydroferulic acid, and quinic acid.

21. A method for preparing a coffee fruit powder, the method comprising drying a coffee fruit extract prepared by the method of claim 1.

22. The method of claim 21, wherein drying the coffee fruit extract is performed using a pulse drying system.

23. A coffee fruit extract prepared by the method of claim 1.

24. A composition comprising the coffee fruit extract of claim 23.

25. The composition of claim 24, wherein the composition is a dietary supplement, snack bar, neutraceutical, juice, sports drink, carbonated beverage, or tea.

26. The composition of claim 24, wherein the composition is a skin care product, anti-aging product, or other cosmetic product.

\* \* \* \* \*

UNITED STATES PATENT AND TRADEMARK OFFICE
CERTIFICATE OF CORRECTION

| | |
|---|---|
| PATENT NO. | : 10,709,149 B2 |
| APPLICATION NO. | : 15/766738 |
| DATED | : July 14, 2020 |
| INVENTOR(S) | : Mark L. Muller |

Page 1 of 1

It is certified that error appears in the above-identified patent and that said Letters Patent is hereby corrected as shown below:

In the Claims

At Column 28, Claim number 5, Line number 25, delete "The method claim 1, further comprising" replace with --The method of claim 1, further comprising--

Signed and Sealed this
Twenty-second Day of December, 2020

Andrei Iancu
*Director of the United States Patent and Trademark Office*